(12) United States Patent
Wasserman et al.

(10) Patent No.: US 12,702,829 B2
(45) Date of Patent: Aug. 11, 2026

(54) TRANSDUCER ARRAY HAVING A TEMPERATURE SENSOR ISOLATION LAYER BETWEEN A TEMPERATURE SENSOR AND EXTERNAL ENVIRONMENT

(71) Applicant: Novocure GmbH, Root (CH)

(72) Inventors: Yoram Wasserman, Haifa (IL); Aharon Levy, Haifa (IL)

(73) Assignee: Novocure GmbH, Baar (CH)

( * ) Notice: Subject to any disclaimer, the term of this patent is extended or adjusted under 35 U.S.C. 154(b) by 196 days.

(21) Appl. No.: 18/477,197

(22) Filed: Sep. 28, 2023

(65) Prior Publication Data

US 2024/0108893 A1 Apr. 4, 2024

Related U.S. Application Data

(60) Provisional application No. 63/377,605, filed on Sep. 29, 2022.

(51) Int. Cl.
*A61N 1/04* (2006.01)
*A61N 1/08* (2006.01)
(Continued)

(52) U.S. Cl.
CPC ....... *A61N 1/36002* (2017.08); *A61N 1/0476* (2013.01); *A61N 1/08* (2013.01)

(58) Field of Classification Search
CPC .... A61N 1/36002; A61N 1/0476; A61N 1/08; A61N 1/40; A61N 1/0492; A61N 1/328;
(Continued)

(56) References Cited

U.S. PATENT DOCUMENTS 5,562,720 A * 10/1996 Stern .................. A61B 18/1485 606/41
8,715,203 B2 5/2014 Palti
(Continued)

FOREIGN PATENT DOCUMENTS

CN 113769267 A 12/2021

OTHER PUBLICATIONS

Raza, M Hassan et al. "Surface Recovery Investigation of Silicone Rubber Composites for Outdoor Electrical Insulation under Accelerated Temperature and Humidity." Polymers vol. 13,18 3024. Sep. 7, 2021, doi:10.3390/polym13183024 (Year: 2021).*
(Continued)

*Primary Examiner* — Carl H Layno
*Assistant Examiner* — Anh-Khoa N Dinh
(74) *Attorney, Agent, or Firm* — DUNLAP CODDING, P.C.

(57) ABSTRACT

A transducer array, tumor treating field system, and method are herein disclosed. The transducer array comprises an electrode having a first side and a second side; a transfer layer covering the first side of the electrode and configured to transfer TTFields into a patient; a temperature sensor in contact with the second side of the at least one electrode; and an isolation layer covering the temperature sensor and at least a portion of the at least one electrode such that the temperature sensor is positioned between the isolation layer and the second side of the electrode, the isolation layer resisting at least one of heat flow and fluid flow through the isolation layer.

20 Claims, 2 Drawing Sheets

(51) Int. Cl.
*A61N 1/36* (2006.01)
*A61N 1/40* (2006.01)

(58) Field of Classification Search
CPC .......... A61N 2007/0034; A61N 5/0616; A61N 1/0452; A61N 1/36034; A61N 7/00; A61N 2005/0643; A61N 2007/0008; A61N 1/0456; A61N 5/0622; A61N 1/0472; A61N 1/05; A61N 1/0587; A61N 1/403; A61N 2005/0652; A61N 1/025; A61N 1/0428; A61N 1/0464; A61N 1/048; A61N 1/0484; A61N 1/205; A61N 1/28; A61N 1/36003; A61N 1/3603; A61N 1/36031
See application file for complete search history.

(56) References Cited

U.S. PATENT DOCUMENTS

2005/0148996 A1* 7/2005 Sun .......................... A61N 1/30 604/20
2007/0150008 A1* 6/2007 Jones .................. A61N 1/0492 604/20
2009/0076363 A1* 3/2009 Bly ........................ A61B 5/282 600/372
2020/0372705 A1* 11/2020 Hershkovich ........... G06T 17/00
2022/0193435 A1 6/2022 Wasserman

OTHER PUBLICATIONS

"Hydrophobic material" [online]. Porex [retrieved Aug. 29, 2025]. Retrieved from the Internet: <URL: https://www.porex.com/porous-polymers-technologies/hydrophobic-materials/ > (Year: 2025).*
Davis, Angela. "What are insulation R-values?" [online]. Insulation & More [retrieved Aug. 29, 2025]. Retrieved from the Internet: <URL: https://insulation-more.co.uk/blogs/the-pipe-duct-lagging-expert/what-are-insulation-r-values (Year: 2025).*
"What Is Polyester Insulation?" [online]. Insulation Essentials [retrieved Aug. 29, 2025]. Retrieved from the Internet: <URL: https://insulationessentials.com.au/what-is-polyester-insulation/?srsltid=AfmBOop1dHu4eNgFv3KHpwkv5A5pfW_3b6nlzmSUz8C0321V2DPDgROG (Year: 2025).*
International Search Report and Written Opinion, dated Dec. 14, 2023, regarding PCT/IB2023/059725, filed Sep. 28, 2023, 11 pages.

* cited by examiner

TRANSDUCER ARRAY HAVING A TEMPERATURE SENSOR ISOLATION LAYER BETWEEN A TEMPERATURE SENSOR AND EXTERNAL ENVIRONMENT

CROSS REFERENCE TO RELATED APPLICATIONS/INCORPORATION BY REFERENCE STATEMENT

The present patent application claims priority to the provisional patent application identified by 63/377,605 filed on Sep. 29, 2022, the entire content of which is hereby incorporated herein by reference.

BACKGROUND

Tumor Treating Fields (TTFields or TTFs) are low intensity (e.g., 1-3 V/cm) alternating electric fields within the intermediate frequency range (e.g., 50 kHz to 1 MHz, such as 50-500 kHz) that target solid tumors by disrupting mitosis. This non-invasive treatment targets solid tumors and is described, for example, in U.S. Pat. Nos. 7,016,725; 7,089,054; 7,333,852; 7,565,205; 8,244,345; 8,715,203; 8,764,675; 10,188,851; and 10,441,776. TTFields are typically delivered through two pairs of transducer arrays that generate perpendicular fields within the treated tumor; the transducer arrays that make up each of these pairs are positioned on opposite sides of the body part that is being treated. More specifically, for the OPTUNE® system, one pair of electrodes of the transducer array is located to the left and right (LR) of the tumor, and the other pair of electrodes of the transducer array is located anterior and posterior (AP) to the tumor. TTFields are approved for the treatment of glioblastoma multiforme (GBM), and may be delivered, for example, via the OPTUNE® system (Novocure Limited, St. Helier, Jersey), which includes transducer arrays placed on the patient's shaved head. More recently, TTFields therapy has been approved as a combination therapy with chemotherapy for malignant pleural mesothelioma (MPM), and may find use in treating tumors in other parts of the body.

The device is intended to be continuously worn by the patient for 2-4 days before removal for hygienic care and re-shaving (if necessary), followed by reapplication with a new set of arrays. Because patients use the device and go about their daily activities, the device may be used for an extended period of time during which the transducer array may generate heat while activated. In order to ensure the patient is comfortable while wearing the transducer arrays, temperature sensors are placed within the arrays to monitor temperatures at the transducer array—skin interface.

SUMMARY OF THE DISCLOSURE

Traditionally, the temperature sensors are placed within a cavity of a transfer layer, i.e., dielectric layer, between an electrode of the transducer array and the patient's skin in order to measure a temperature close to the surface of the patient's skin. Advances in transducer array construction, however, have resulted in transfer layers that, while thinner and lighter, are resistant to forming the void in which to place the temperature sensor, and moving the temperature sensor further from the surface of the patient's skin may result in inaccuracies due to environmental temperature differences. Construction of these types of arrays requires that the temperature sensor is placed further from the transducer array—skin interface (e.g., wherein the electrode is disposed between the temperature sensor and the patient's skin) than is desirable thereby resulting in inaccuracies in temperature measurement by the temperature sensor due to interactions with the external environment.

Thus, new and improved systems that increase temperature measurement accuracy when the electrode element is disposed between the temperature sensor and the patient's skin are desired. It is to such systems and methods of producing and using the same, that the present disclosure is directed The problem of temperature measurement inaccuracies due to environmental temperature differences is solved by a transducer array, tumor treating field system, and method for delivering TTFields to a body of a subject. In one embodiment, the transducer array comprises an electrode having a first side and a second side; a transfer layer covering the first side of the electrode and configured to transfer TTFields into a patient; a temperature sensor in contact with the second side of the at least one electrode; and an isolation layer covering the temperature sensor and at least a portion of the at least one electrode such that the temperature sensor is positioned between the isolation layer and the second side of the electrode, the isolation layer resisting at least one of a heat flow and fluid flow through the isolation layer.

In one embodiment, the tumor treating field system includes an electric field generator configured to generate an electrical signal having an alternating current waveform at a frequency in a range from 50 kHz to 1 MHz; a first conductive lead electrically coupled to the electric field generator, the first conductive lead configured to carry the electrical signal; a first transducer array coupled to the first conductive lead, a second conductive lead electrically coupled to the electric field generator; and a second transducer array coupled to the second conductive lead, the second transducer array receiving the electrical signal from the second conductive lead, and, in conjunction with the first transducer array, forming a tumor treating field. The first transducer array may include at least an electrode layer having a first surface, a second surface and an outer perimeter, a transfer layer in contact with the second surface of the electrode layer, a temperature sensor in contact with the first surface of the electrode layer, and an isolation layer disposed over the temperature sensor and at least a portion of the first surface of the electrode layer, the isolation layer resisting at least one of heat flow and a fluid flow through the isolation layer.

The details of one or more implementations of the subject matter described in this specification are set forth in the accompanying drawings and the description below. Other aspects, features and advantages of the subject matter will become apparent from the description, the drawings, and the claims.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function. In the drawings.

DETAILED DESCRIPTION

Figure 1:
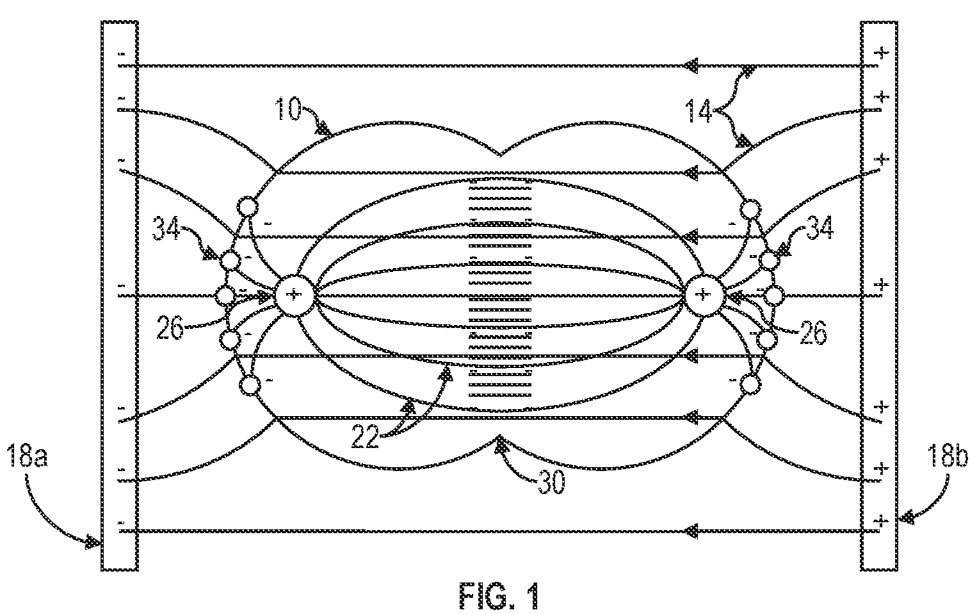
FIG. 1 is an exemplary embodiment of a schematic diagram of electrodes as applied to living tissue.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Headings are provided for convenience only and are not to be construed to limit the disclosure in any manner. Embodiments illustrated under any heading or in any portion of the disclosure may be combined with embodiments illustrated under the same or any other heading or other portion of the disclosure. Any combination of the elements described herein in all possible variations thereof is encompassed by the disclosure unless otherwise indicated herein or otherwise clearly contradicted by context.

Unless otherwise required by context, singular terms shall include pluralities and plural terms shall include the singular.

All of the compositions, assemblies, systems, kits, and/or methods disclosed herein can be made and executed without undue experimentation in light of the present disclosure. Where a method claim does not specifically state in the claims or description that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of embodiments described in the specification.

The use of the term "a" or "an" when used in conjunction with the term "comprising" in the claims and/or the specification may mean "one," but is also consistent with the meaning of "one or more," "at least one," and "one or more than one." The term "plurality" refers to "two or more."

In addition, the use of the term "at least one of X, Y, and Z" will be understood to include X alone, Y alone, and Z alone, as well as any combination of X, Y, and Z. The use of ordinal number terminology (e.g., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive.

Circuitry, as used herein, may be analog and/or digital components, or one or more suitably programmed processors (e.g., microprocessors) and associated hardware and software, or hardwired logic. Also, "components" may perform one or more functions. The term "component," may include hardware, such as a processor (e.g., microprocessor), an application specific integrated circuit (ASIC), a field programmable gate array (FPGA), a combination of hardware and software, and/or the like. The term "processor" as used herein means a single processor or multiple processors working independently or together to collectively perform a task.

As used herein, all numerical values or ranges include fractions of the values and integers within such ranges and fractions of the integers within such ranges unless the context clearly indicates otherwise. The numerical ranges specified herein includes the endpoints, and all values, sub-ranges of values within the range, and fractions of the values and integers within said range. Thus, any two values within the range of 1 mm to 10 m, for example, can be used to set a lower and an upper boundaries of a range in accordance with the embodiments of the present disclosure.

As used herein, the term TTField (TTFields, or TTF(s)) refers to low intensity (e.g., 1-4 V/cm) alternating electric fields of medium frequencies (about 50 kHz-1 MHz, and more preferably from about 50 kHz-500 kHz) that when applied to a conductive medium, such as a human body, via electrodes may be used, for example, to treat tumors as described in U.S. Pat. Nos. 7,016,725, 7,089,054, 7,333,852, 7,565,205, 7,805,201, and 8,244,345 by Palti) and in a publication by Kirson (see Eilon D. Kirson, et al., Disruption of Cancer Cell Replication by Alternating Electric Fields, Cancer Res. 2004 64:3288-3295). TTFields have been shown to have the capability to specifically affect cancer cells and serve, among other uses, for treating cancer. TTFields therapy is an approved mono-treatment for recurrent glioblastoma (GBM), and an approved combination therapy with chemotherapy for newly diagnosed GBM patients.

As used herein, the term TTSignal is an electrical signal that, when received by electrodes applied to a conductive medium, such as a human body, causes the electrodes to generate the TTField described above. The TTSignal is often an AC electrical signal.

Referring now to the drawings and in particular to FIG. 1, shown therein is an exemplary embodiment of a dividing cell 10, under the influence of external TTFields, generally indicated as lines 14, generated by a first electrode **18*a* having a negative charge and a second electrode 18*b* having a positive charge. Further shown are microtubules 22 that are known to have a very strong dipole moment. This strong polarization makes the microtubules 22, as well as other polar macromolecules and especially those that have a specific orientation within the cell 10 or its surroundings, susceptible to electric fields. The microtubules 22 positive charges are located at two centrioles 26 while two sets of negative poles are at a center 30 of the dividing cell 10 and point of attachment 34 of the microtubules 22** to the cell membrane. The locations of the charges form sets of double dipoles and therefore are susceptible to electric fields of differing directions. In one embodiment, the cells go through electroporation, that is, DNA or chromosomes are introduced into the cells using a pulse of electricity to briefly open pores in the cell membranes.

Figure 2:
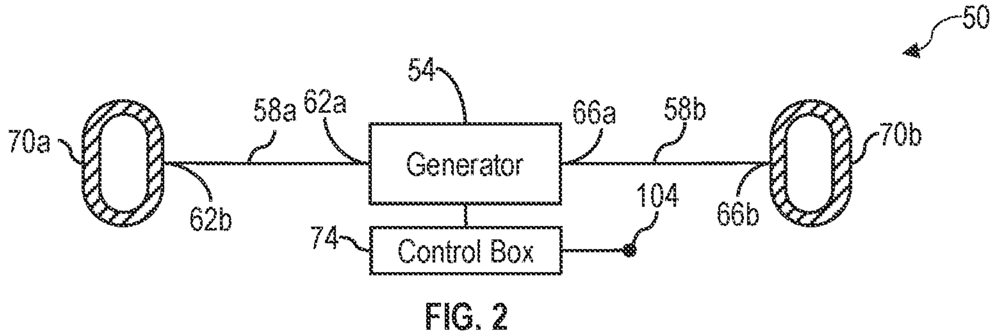
FIG. 2 is an exemplary embodiment of an electronic device configured to generate a TTField constructed in accordance with the present disclosure.

Turning now to FIG. 2, the TTFields described above that have been found to advantageously destroy tumor cells may be generated by an electronic apparatus 50. FIG. 2 is a simple schematic diagram of the electronic apparatus 50 illustrating major components thereof. The electronic apparatus 50 includes an electric field generator 54 and a pair of conductive leads 58, including first conductive lead 58*a* and second conductive lead 58*b*. The first conductive lead 58*a* includes a first end 62*a* and a second end 62*b*. The second conductive lead 58*b* includes a first end 66*a* and a second end 66*b*. The first end 62*a* of the first conductive lead 58*a* is conductively attached to the electric field generator 54 and the first end 66*a* of the second conductive lead 58*b* is conductively attached to the electric field generator 54.

The electric field generator 54 is configured to supply power and generate desirable electric signals (TTSignals) in the shape of waveforms or trains of pulses as an output. The second end 62*b* of the first conductive lead 58*a* is connected to a transducer array 70*a* and the second end 66*b* of the second conductive lead 58*b* is connected to a transducer array 70*b*. Both of the transducer array 70*a* and the transducer array 70*b* are supplied with the electric signals (e.g., TTSignals, wave forms). The transducer array 70*a* and the transducer array 70*b*, being supplied with the electric signals, causes an electrical current to flow between the transducer array 70*a* and the transducer array 70*b*. The electrical current generates an electric field (i.e., TTField), having a frequency and an amplitude, to be generated between the transducer array 70*a* and the transducer array 70*b*.

While the electronic apparatus 50 shown in FIG. 2 comprises only two transducer arrays 70 (i.e., the transducer array 70*a* and the transducer array 70*b*), in some embodiments, the electronic apparatus 50 may comprise more than two transducer arrays 70.

The electric field generator 54 generates an alternating voltage wave form (i.e., TTSignal) at frequencies in the range from about 50 kHz to about 1 MHz (preferably from about 100 kHz to about 500 kHz). The required voltages are such that an electric field intensity in tissue within the treatment area is in the range of about 0.1 V/cm to about 10 V/cm. To achieve this electric field intensity, the potential difference between the two conductors 18 (e.g., the electrode element 78 in FIG. 3) in each of the transducer array 70*a* or the transducer array 70*b* is determined by the relative impedances of the system components, e.g., a fraction of the electric field on each component is given by that component's impedance divided by a total circuit impedance.

In certain particular (but non-limiting) embodiments, the transducer array 70*a* and the transducer array 70*b* generate an alternating electric current and field within a target region of a patient. The target region typically comprises at least one tumor, and the generation of the alternating electric current and field selectively destroys and/or inhibits growth of the tumor. The alternating electric current and field may be generated at any frequency that selectively destroys or inhibits growth of the tumor, such as at any frequency of a TTField.

In certain particular (but non-limiting) embodiments, the alternating electric current and field may be imposed at two or more different frequencies. When two or more frequencies are present, each frequency is selected from any of the above-referenced values, or a range formed from any of the above-referenced values, or a range that combines two integers that fall between two of the above-referenced values.

In order to optimize the electric field (i.e., TTField) distribution, the transducer array 70*a* and the transducer array 70*b* (pair of transducer arrays 70) may be configured differently depending upon the application in which the pair of transducer arrays 70 are to be used. The pair of transducer arrays 70, as described herein, are externally applied to a patient, that is, are generally applied to the patient's skin, in order to apply the electric current, and electric field (TTField) thereby generating current within the patient's tissue. Generally, the pair of transducer arrays 70 are placed on the patient's skin by a user such that the electric field is generated across patient tissue within a treatment area. TTFields that are applied externally can be of a local type or widely distributed type, for example, the treatment of skin tumors and treatment of lesions close to the skin surface.

In one embodiment, the user may be a medical professional, such as a doctor, nurse, therapist, or other person acting under the instruction of a doctor, nurse, or therapist. In another embodiment, the user may be the patient, that is, the patient (and/or a helper) may place the transducer array 70*a* and the transducer array 70*b* on the patient's treatment area.

According to another exemplary embodiment, the electronic apparatus 50 includes a controller 74. In one embodiment, the controller 74 comprises circuitry configured to control the output of the electric field generator 54, for example, to set the output at the maximal value that does not cause excessive heating of the treatment area. The controller 74 may issue a warning, or the like, when a temperature of the treatment area (as sensed by one or more of a plurality of temperature sensors 104, discussed in more detail below) exceeds a preset limit. The temperature sensors may be mechanically connected to and/or otherwise associated with the transducer array 70*a* and/or the transducer array 70*b* so as to sense the temperature of the treatment area at either one or both of the transducer array 70*a* or the transducer array 70*b* as described below in more detail.

In one embodiment, the controller 74 may turn off, or decrease power of the TTSignal generated by the electric field generator 54, if a temperature sensed by the temperature sensor 104 meets or exceeds a comfortability threshold. In one embodiment, the comfortability threshold is the temperature at which a patient would be made uncomfortable while using the transducer array 70*a* and the transducer array 70*b*. For example, the comfortability threshold may be a temperature at or about 40 degrees Celsius. In one embodiment, the comfortability threshold is a temperature of between about 39 degrees Celsius and 42 degrees Celsius, or a specific selected temperature between about 39 degrees Celsius and 42 degrees Celsius.

The conductive leads 58 are isolated conductors with a flexible metal shield, preferably grounded thereby preventing spread of any electric field generated by the conductive leads 58. The transducer array 70*a* and the transducer array 70*b* may have specific shapes and positioning so as to generate the TTField of a desired configuration, direction, and intensity at the treatment area and only at that treatment area so as to focus the treatment.

The specifications of the electronic apparatus 50 as a whole and its individual components are largely influenced by the fact that at the frequency of the TTFields, living systems behave according to their "Ohmic", rather than their dielectric properties.

Figure 3:
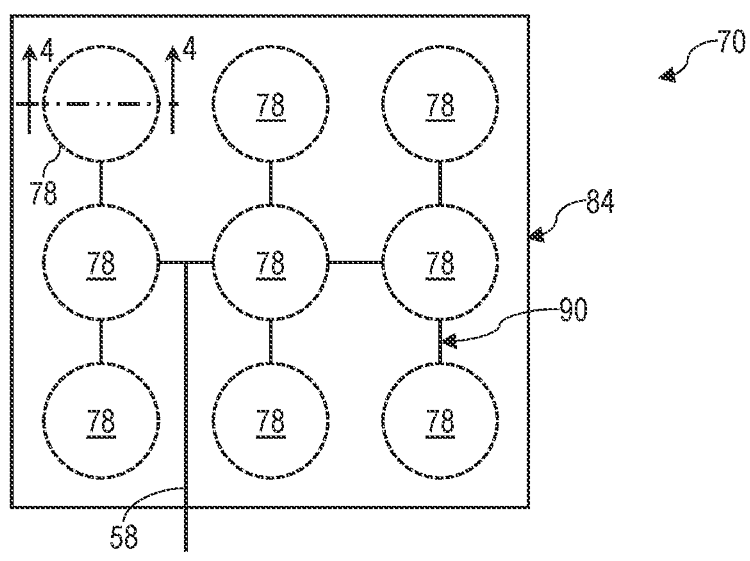
FIG. 3 is a block diagram of an exemplary embodiment of a transducer array constructed in accordance with the present disclosure.

Referring now to FIG. 3, shown therein is a diagram of an exemplary embodiment of the transducer array 70 constructed in accordance with the present disclosure. The transducer array 70 includes one or more electrode element 78. As shown in FIG. 3, each transducer array 70 is configured as a set of one or more electrode elements 78. In the example shown, the transducer array 70 includes 9 electrode elements 78. Transducer arrays 70 may utilize electrode elements 78 that are capacitively coupled. In the example shown in FIG. 3, the transducer array 70 is configured as multiple electrode elements 78 (for example, about 2 cm in diameter) that are interconnected via flex wires 90 (and connected to the electric field generator 54 via the conductive lead 58). Each electrode element 78 is discussed in more detail below and shown in FIG. 4. In one embodiment, the transducer array 70 includes an outer peripheral edge 84.

Figure 4:
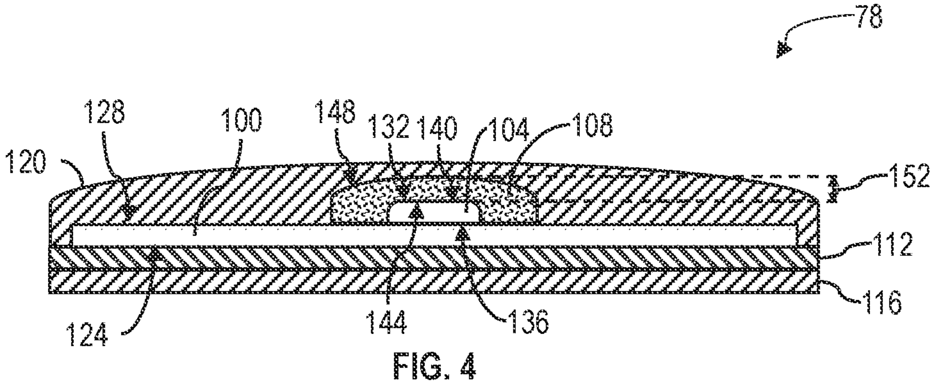
FIG. 4 is a cross-sectional diagram of an electrode element of the transducer array depicted in FIG. 3 taken along the lines 4-4 in FIG. 3.

Referring now to FIG. 4, shown therein is a cross-sectional diagram of an exemplary embodiment of one of the electrode elements 78 of FIG. 3 constructed in accordance with the present disclosure. The electrode element 78 generally comprises an electrode 100, a temperature sensor 104, an isolation layer 108, and a transfer layer 112. In some embodiments, the electrode element 78 further comprises a patient interface member 116 and/or a top-coat layer 120.

The electrode 100 comprises and/or consists of at least one conducting element and/or compound, including, by way of example only, elemental silver. In some embodiments, the electrode 100 further includes a conductive support layer electrically coupled to the electrode 100. The electrode 100 may be selected from any conductive material having desirable properties such as, but not limited to, high conductivity, strong biocompatibility, and low reactivity with other layers or components of the transducer array 70. When present, the conductive support layer may be formed of a conductive carbon film, or conductive fabric, configured to support the electrode 100. In one embodiment, the conductive support layer may be electroplated or otherwise bonded to the electrode 100.

In one embodiment, the electrode 100 is electrically conductive and comprises, at least in part, a material selected from one or more of the following: silver, tin, aluminum, titanium, platinum, an alloy thereof, and/or some combination thereof.

The electrode 100 further includes a first surface 124 and a second surface 128. The temperature sensor 104 may be in contact with and supported by the second surface 128 of the electrode 100 such that the temperature sensor 104 may detect and/or correspond to a temperature experienced by the patient where the electrode 100 is placed. In some embodiments, the first surface 124 of the electrode 100 is in contact with the transfer layer 112 when the transfer layer 112 is present.

In one embodiment, the temperature sensor 104 may comprise an outer surface 132, wherein any environment, or atmosphere, in contact with the outer surface 132 of the temperature sensor 104 affects a temperature of the temperature sensor 104. The outer surface 132 of the temperature sensor 104 may be considered to have at least two surface portions: a contact portion 136, e.g., a surface portion of the outer surface 132 in contact with the second surface 128 of the electrode 100, and an exposed portion 140, e.g., a surface of the outer surface 132 that is not in contact with the second surface 128 of the electrode 100.

In some embodiments, the temperature sensor 104 comprises a thermistor wherein a temperature of the thermistor may be determined by routing a known current through the thermistor and measuring a voltage that appears across the thermistor. In one embodiment, the temperature sensor 104 is mechanically connected to and/or otherwise associated with a particular one of the electrode element(s) 78 of the transducer array 70 so as to infer a temperature of the treatment area at the particular one or more electrode element 78 location.

In one embodiment, the isolation layer 108 has a first surface 144 and a second surface 148 and comprises a thermal insulator operable to resist a transfer of heat through the thermal insulator and/or a water-resistant material operable to resist a transfer of fluid, e.g., gas or liquid through the water-resistant material. For example, the isolation layer 108 resists heat transfer from the temperature sensor to the environment more than that of a standard bandage. In one embodiment, the isolation layer 108 resists heat flow and fluid flow and comprises a thermally insulating matrix material, such as, for example, a thermally insulating foam material or an epoxy material. The thermally insulation matrix material may also be a hydrophobic and thermally insulating matrix material, epoxy material, or a liquid resistant matrix material. The fluid flow can be a liquid flow and/or a gas flow. An example of a gas flow is a flow of air containing water vapor. In some embodiments, the isolation layer 108 may be constructed of a non-epoxy material having insulating properties such as the foam materials described herein as well as water proof sealants (e.g., silicone water proof sealant, liquid rubber, and the like), waterproof fabric such as a synthetic rubber that may be produced by polymerization of chloroprene (e.g., neoprene) or the like.

An exemplary thermally insulating and hydrophobic foam material includes a closed cell foam, such as a closed cell polyethylene foam, which may be coated with a pressure sensitive adhesive so as to bond the isolation layer 108 to the electrode 100. In some embodiments, the isolation layer 108 has a thickness of 0.9 mm. In some embodiments, the isolation layer 108 can be constructed of a medical foam tape identified by model no. 1773 obtainable from the 3M Company of Saint Paul Minnesota in the United States.

An exemplary epoxy material may include a two-part epoxy resin. The epoxy material may be an epoxy, a polyester resin, and/or an epoxy acrylate. Prior to polymerization/polymer crosslinking, one or more component of the epoxy may be combined with a thermal insulation component to impart desirable thermal insulation properties into the polymerized epoxy and/or a water-resistant component to impart desirable hydrophobic properties into the epoxy.

In one embodiment, the isolation layer 108 is air-impermeable to prevent, limit, and/or minimize exposure of the temperature sensor 104 to the environment, or atmosphere. That is, the isolation layer 108 prevents, limits, and/or minimizes air from moving between the second surface 148 of the isolation layer 108 and the first surface 144 of the isolation layer 108.

In one embodiment, the isolation layer 108, when placed on the temperature sensor 104 such that the first surface 144 substantially covers the exposed portion 140 of the outer surface 132, resists heat flow and liquid flow between the temperature sensor 104 and an environment, or atmosphere, on the second surface 148 of the isolation layer 108.

In one embodiment, the first surface 144 of the isolation layer 108 substantially surrounds and is in contact with the exposed portion 140 of the outer surface 132, e.g., the outer surface 132 of the temperature sensor 104 excepting the contact portion 136 of the outer surface 132 that is in contact with the electrode 100. By substantially surrounding and being in contact with the exposed portion 140, the isolation layer 108 thermally isolates the temperature sensor 104 from the environment, or atmosphere, in contact with the second surface 148 of the isolation layer 108.

In one embodiment, the isolation layer 108 is constructed of more than one insulating material. For example, the isolation layer 108 may be comprised of a first insulating material in contact with the temperature sensor 104, and a second insulating material disposed against the first insulating material and exposed to the environment, or atmosphere. In some embodiments, the first insulating material and the second insulating material are composed of the same insulating material but have differing insulating characteristics, the first insulating material and the second insulating material are composed of differing insulating materials but have similar insulating characteristics, or some combination thereof. For example, the first insulating material may be an insulating foam material having a first insulating value while the second insulating material may be an insulating epoxy material having a second insulating value the same as the first insulating value. Conversely, the first insulating material may be an insulating epoxy material having a first insulating value and the second insulating material may be an insulating epoxy material having a second insulating value different from the first insulating value.

In one embodiment, the isolation layer 108 may be constructed of more than one material having different properties. For example, the isolation layer 108 may be comprised of a first isolating material having a thermal insulation property (resisting thermal transfer through the isolation layer 108) and a second isolating material having a water-repellant and/or hydrophobic property (resisting liquid/fluid transfer through the isolation layer 108). The first isolation material and the second isolation material may be disposed in layers over the temperature sensor 104 and, in some embodiments, below the top-coat layer 120.

In one embodiment, the isolation layer 108 covers the temperature sensor and only a portion of the second side of the electrode 100, e.g., the isolation layer 108 does not extend across the entirety of the second surface 128 of the electrode 100. In some embodiments, a first surface area of the first surface 144 of the isolation layer 108 is less than twice a second surface area of the exposed portion 140 of the outer surface 132 of the temperature sensor 104. In other embodiments, the first surface area of the first surface 144 of the isolation layer 108 is less than 20% of a surface area of the second surface 128 of the electrode 100. In yet other embodiments, the first surface area of the first surface 144 of the isolation layer 108 is less than 50% of the surface area of the second surface 128 of the electrode 100.

In one embodiment, the isolation layer 108 has a thickness 152 of between 0.9 mm-1 cm and generally between 0.9 mm-5 mm. In one embodiment, the top coat layer 120 may have a thickness of 0.3 mm-0.4 mm. In one embodiment, the isolation layer 108 has a thickness at least twice as thick as the top-coat layer 120. In other embodiments, the isolation layer 108 has a thickness between 2 times the thickness of the top-coat layer and 6 times the thickness of the top-coat layer 120. In yet other embodiments, the isolation layer 108 has a thickness of 4-6 times the thickness of the top-coat layer 120. In some embodiments, the top coat layer 120 may be a non-conductive top-coat layer.

In one embodiment, to limit and/or prevent shorting out the isolation layer 108 and/or the electrode 100, the isolation layer 108 is not electrically conductive, e.g., is non-conducting. The isolation layer 108, being non-conductive, may increase safety of the electrode element 78 by preventing the patient, or other user, from coming into contact with the thermistor during operation of the transducer array 70 and electronic apparatus 50.

In one embodiment, the isolation layer 108 is hydrophobic, i.e., resists a flow of fluid, e.g., liquid and/or gas through the isolation layer 108. The isolation layer 108 may be constructed of a water impermeable material, a hydrophobic material, a water-resistant material, and/or a water-repellant material. In one embodiment, the isolation layer 108 restricts moisture of the environment from contacting the temperature sensor 104. In some embodiments, the isolation layer 108 does not include any perforation, channel, or other opening through which a liquid might travel.

In one embodiment, the isolation layer 108 is air-impermeable, that is, the isolation layer 108 restricts air transfer through the isolation layer 108 such that air from the environment is restricted from contact with the temperature sensor 108. In some embodiments, the isolation layer 108 does not include any perforation, channel, or other opening through which air might travel.

In one embodiment, when the isolation layer 108 is applied to the transducer array 70 having a plurality of electrode elements 78 each having an electrode 100, the isolation layer 108 comprises a plurality of isolation sections with at least some of the isolation sections disposed over each the temperature sensor 104 and second surface 128 of each electrode 100 of the plurality of electrode elements 78 to separately isolation each of the temperature sensors 104. In some embodiments, when one or more particular electrode 100 of the plurality of electrode elements 78 is not in contact with the temperature sensor 104, the isolation layer 108 may either be excluded from that particular electrode 100 or may be placed on the second surface 128 of the electrode 100 without the temperature sensor 104 disposed therein.

In one embodiment, the transfer layer 112 covers the first surface 124 of the electrode 100 and is configured to transfer TTFields into the patient. In some embodiments, the transfer layer 112 is non-electrically conductive. For example, the transfer layer 112 may include a dielectric layer such as a ceramic disk and/or a high-dielectric, or non-conductive, thin-film polymer layer.

Alternative constructions for the transfer layer 112 may be used, including, for example, ceramic elements that are disc-shaped, ceramic elements that are not disc-shaped, and non-ceramic dielectric materials disposed adjacent the first surface 124 of the electrode 100. In some embodiments, the transfer layer 112 extends beyond the electrode 100 to the outer peripheral edge 84 of the transducer array 70. Exemplary non-ceramic dielectric materials positioned over a plurality of electrode 100 include: polymer films, such as a non-conductive, thin-film high-dielectric polymer.

In some embodiments, the transducer array 70 includes one or more electrode element 78 that is not capacitively coupled to the patient. In this situation, each electrode element 78 of the transducer array 70 may be implemented using the transfer layer 112 comprising a conductive material that is configured for placement against a person's body, with no insulating dielectric layer disposed between the electrode elements 78 and the transfer layer 112. Examples of the conductive material include a conductive film, conductive foam and/or a conductive fabric. Other alternative constructions for implementing the transducer array 70 may also be used, as long as they are capable of delivering TTFields to the patient's body.

In one embodiment, the patient interface member 116 is optional, that is, some embodiments of the transducer array 70 do not include the patient interface member 116. When present, the patient interface member 116 may be disposed between the transfer layer 112 and the patient's body in any of the embodiments described herein.

In one embodiment, the patient interface member 116 is electrically conductive and biocompatible when used for an extended period of time. In one embodiment, the patient interface member 116 is a gel layer, or a hydrogel layer, constructed in accordance with the gel/hydrogel layers described in U.S. Patent Publication No. 2021/0346693 A1, published Nov. 11, 2021 and entitled "CONDUCTIVE PAD GENERATING TUMOR TREATING FIELD AND METHODS OF PRODUCTION AND USE THEREOF" and U.S. Pat. No. 11,458,298, issued on Oct. 4, 2022, and entitled "ASSEMBLIES CONTAINING TWO CONDUCTIVE GEL COMPOSITIONS AND METHODS OF PRODUCTION AND USE THEREOF".

In one embodiment, the patient interface member 116 comprises one or more layer of material configured to be one or more of electrically conductive, biocompatible when in contact with the patient's skin for an extended period of time, e.g., from 3 hours to a week at a time, flexible so as to not impede movement of the patient while the transducer array 70 is in place, and resistant to movement on the patient's skin as the patient goes about their daily routine.

In one embodiment, the patient interface member 116 is constructed of one or more layers of conductive carbon adhesive and graphite/anisotropic materials. Exemplary patient interface members 116 may be constructed in accordance with U.S. patent application Ser. No. 17/899,220, filed Aug. 30, 2022 and entitled "ELECTRODE ASSEMBLY WITH A SKIN CONTACT LAYER COMPRISING A CONDUCTIVE ADHESIVE COMPOSITE, AND SYSTEMS AND METHODS OF APPLYING TUMOR TREATING FIELDS USING SAME".

In some embodiments, the patient interface member 116 extends as far as the electrode 100 whereas in other embodiments, the patient interface member 116 extends at least to the outer peripheral edge 84 of the transducer array 70 or beyond.

In one embodiment, the top-coat layer 120 may increase safety of the transducer array 70 and/or electrode element 78 by preventing or limiting contact with the electrode 100 to guard against accidental electrocution when the electrode element 78 is activated. The top-coat layer 120 may be constructed of a durable, non-conductive material, such as a non-conductive fabric. In some embodiments, the non-conductive fabric may have a plurality of perforations. In one embodiment, the top-coat layer has a thickness of less than 1 mm and generally has a thickness of about 0.5 mm.

In one embodiment, the top-coat layer 120 may extend within the outer peripheral edge 84 of the transducer array 70 or beyond and may have an extent similar to that of the patient interface member 116. In some embodiments, the top-coat layer 120 extends to cover the second surface 128 of the electrode 100. In one embodiment, the top-coat layer 120 may extend beyond any other component of the transducer array 70 and, having an adhesive on a surface of the top-coat layer 120, adhere to the patient's skin to prevent the transducer array 70 and/or electrode element 78 from moving relative to the patient's skin once placed on the patient.

In one embodiment, the top-coat layer 120 has an insulation value that is lesser than the insulation value of the isolation layer 108. The insulation value of the top-coat layer 120 may be in a range from ½ to ¼ of the insulation value of the isolation layer 108.

Figure 5:
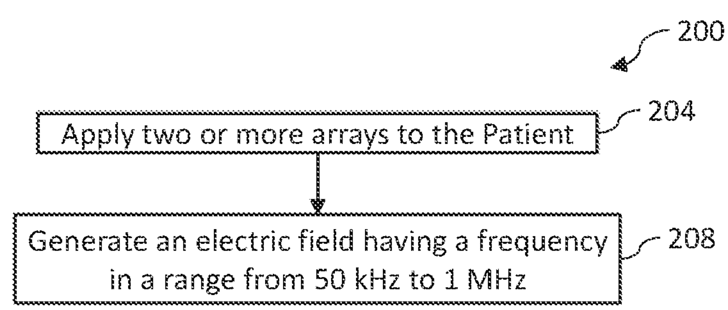
FIG. 5 is a flow diagram of an exemplary embodiment for providing TTFields to a patient in accordance with the present disclosure.

Referring now to FIG. 5, shown therein is an exemplary embodiment of a process 200 of using the electronic apparatus 50 and the transducer array 70 to apply a TTField to a patient in accordance with the present disclosure. The process 200 generally comprises the steps of: applying the transducer array 70*a* and the transducer array 70*b* to the Patient (step 204) and generating an alternating electric field having a frequency in a range of from about 50 kHz to about 1 MHz for a period of time (step 208).

The step of applying the transducer array 70*a* and the transducer array 70*b* to the Patient (step 204) may be performed by the user. In one embodiment, before applying the transducer array 70*a* to the patient's skin, the patient's skin may need to be cleaned (e.g., such as but not limited to, cleansing of the skin of foreign matter or biological matter and shaving of the skin, if necessary) to enable the transducer array 70*a* to adhere to the patient's skin.

The step of generating an alternating electric field (TTField) (step 208) may be performed by the electric field generator 54 and may be instantiated by an operation performed by the user or controller 74. In one embodiment, step 208 may be performed more than one time and the period of time for which the step 208 is performed a first time may be the same as or different from the period of time for which the step 208 is performed a second time (or other period(s) of time beyond the second time). In some embodiments, step 208 is only performed once before the process 200 is repeated. There may be a time period between each time the process 200 is repeated. Each time the process 200 is repeated, the time period may be the same as or different from the previous time period. Each time the process 200 is repeated, the first conductive pad 100*a* and the second conductive pad 100*b* may be placed in the same or a different position on the patient's skin.

The step of generating an alternating electric field (TTField) (step 208) may be performed by generating the alternating electric current and field at two or more different frequencies within the range of 50 kHz to 1 MHz. When two or more frequencies are present, each frequency is selected from any of the above-referenced values, or a range formed from any of the above-referenced values, or a range that combines two integers that fall within the range of the above-referenced values.

In one embodiment, the step of generating an alternating electric field (TTField) (step 208) may be performed by supplying a first alternating electric current and field to a first pair of transducer arrays 70 for a first period of time and supplying a second alternating electric current and field to a second pair of transducer arrays 70 for a second period of time. In one embodiment, the first period of time may be of a similar duration to the second period of time whereas in other embodiments, the first period of time may be of a different duration to the second period of time. Additionally, the first period of time may or may not overlap with the second period of time.

ILLUSTRATIVE EMBODIMENTS

The following is a number list of non-limiting illustrative embodiments of the inventive concept disclosed herein:

1. A transducer array, comprising:

an electrode having a first side and a second side;

a transfer layer covering the first side of the electrode and configured to transfer TTFields into a patient;

a temperature sensor in contact with the second side of the electrode; and an isolation layer covering the temperature sensor and at least a portion of the electrode such that the temperature sensor is positioned between the isolation layer and the second side of the electrode, the isolation layer resisting at least one of a heat flow and fluid flow through the isolation layer.

2. The transducer array of illustrative embodiment 1, further comprising a top-coat layer disposed over the isolation layer and an exposed portion of the second side of the electrode not in contact with the temperature sensor and the isolation layer, the top-coat layer having a first thickness lesser than a second thickness of the isolation layer.

3. The transducer array of illustrative embodiment 2, wherein the isolation layer has the second thickness in a range of 2-6 times thicker than the first thickness of the top-coat layer.

4. The transducer array of any of illustrative embodiments 1-3, wherein the isolation layer is a thermal insulator.

5. The transducer array of illustrative embodiment 2, wherein the isolation layer comprises a thermally insulating matrix material, the thermally insulating matrix material configured to resist a heat flow from the temperature sensor to an atmosphere outside of the isolation layer more than that of a the top-coat layer.

6. The transducer array of any of illustrative embodiments 1-5, wherein the isolation layer comprises a liquid resistant matrix material, the liquid resistant matrix material configured to resist a liquid flow through the isolation layer.

7. The transducer array of illustrative embodiment 6, wherein the isolation layer is hydrophobic.

8. The transducer array of any of illustrative embodiments 1-7, wherein the isolation layer covers the temperature sensor and only a portion of the second side of the electrode.

9. The transducer array of illustrative embodiment 8, wherein the isolation layer covers the temperature sensor and is in contact with less than 20% of the second side of the electrode.

10. The transducer array of any of illustrative embodiments 1-9, wherein the isolation layer comprises at least one of an epoxy material, a thermally insulating foam material, and a hydrophobic material.

11. The transducer array of any of illustrative embodiments 1-19, wherein the isolation layer is non-conducting.

12. The transducer array of any of illustrative embodiments 1-12, wherein the transfer layer is a non-conductive, thin-film polymer layer.

13. The transducer array of any of illustrative embodiments 1-12, wherein the temperature sensor is a thermistor.

14. The transducer array of any of illustrative embodiments 1-13, wherein the isolation layer has a first insulation value, and wherein the electrode has an outer perimeter, and further comprising a non-conductive top-coat layer disposed on the isolation layer, the non-conductive top-coat layer extending within the outer perimeter and beyond the outer perimeter of the electrode, the non-conductive top-coat layer having a second insulation value less than the first insulation value.

15. The transducer array of any of illustrative embodiments 1-14, further comprising a patient interface member covering the transfer layer such that the transfer layer is positioned between the patient interface member and the first side of the electrode, the patient interface member being configured for placement between the transfer layer and a patient's skin.

16. A tumor treating field system, comprising:

an electric field generator configured to generate an electrical signal having an alternating current waveform at a frequency in a range from 50 kHz to 1 MHz;

a first conductive lead electrically coupled to the electric field generator, the first conductive lead configured to carry the electrical signal;

a first transducer array coupled to the first conductive lead, the first transducer array comprising at least an electrode layer having a first surface, a second surface and an outer perimeter, a transfer layer in contact with the first surface of the electrode layer, a temperature sensor in contact with the second surface of the electrode layer, and an isolation layer disposed over the temperature sensor and at least a portion of the second surface of the electrode layer, the isolation layer resisting at least one of a heat flow and a fluid flow through the isolation layer;

a second conductive lead electrically coupled to the electric field generator; and a second transducer array coupled to the second conductive lead, the second transducer array receiving the electrical signal from the second conductive lead, and, in conjunction with the first transducer array, forming a tumor treating field.

17. The tumor treating field system of illustrative embodiment 16, wherein the first transducer array further comprising a top-coat layer disposed over the isolation layer and an exposed portion of the second surface of the electrode layer not in contact with the temperature sensor and the isolation layer, the top-coat layer having a first thickness lesser than a second thickness of the isolation layer.

18. The tumor treating field system of any of illustrative embodiments 16-17, wherein the isolation layer has a first insulation value, and wherein the first transducer array further comprises a non-conductive top-coat layer disposed on the isolation layer, the non-conductive top-coat layer extending within the outer perimeter and beyond the outer perimeter of the electrode layer, the non-conductive top-coat layer having a second insulation value less than the first insulation value.

19. The tumor treating field system of any of illustrative embodiments 16-18, wherein the transfer layer is a non-conductive, thin-film polymer layer.

20. The tumor treating field system of any of illustrative embodiments 16-19, wherein the electrode layer of the first transducer array comprises a plurality of electrodes, each electrode comprising a first surface and a second surface and having a temperature sensor in contact with the first surface, and wherein the isolation layer includes a plurality of isolation sections with at least some of the isolation sections disposed over the temperature sensors and at least a portion of the first surface of each electrode.

21. The tumor treating field system of any of illustrative embodiments 16-20, wherein the isolation layer comprises a thermally insulating matrix material, the thermally insulating matrix material configured to resist a heat flow from the temperature sensor to an atmosphere outside of the isolation layer more than that of a the top-coat layer.

22. The tumor treating field system of any of illustrative embodiments 16-21, wherein the isolation layer comprises a liquid resistant matrix material, the liquid resistant matrix material configured to resist a liquid flow through the isolation layer.

23. The tumor treating field system of any of illustrative embodiments 16-22, wherein the isolation layer is non-conducting.
24. The tumor treating field system of any of illustrative embodiments 16-23, wherein the transfer layer includes a high-dielectric polymer film.
25. The tumor treating field system of any of illustrative embodiments 16-24, wherein the temperature sensor is a thermistor.

From the above description, it is clear that the inventive concepts disclosed and claimed herein are well adapted to carry out the objects and to attain the advantages mentioned herein, as well as those inherent in the disclosure. While exemplary embodiments of the inventive concepts have been described for purposes of this disclosure, it will be understood that numerous changes may be made which will readily suggest themselves to those skilled in the art and which are accomplished within the spirit of the inventive concepts disclosed and claimed herein.

The foregoing description provides illustration and description, but is not intended to be exhaustive or to limit the inventive concepts to the precise form disclosed. Modifications and variations are possible in light of the above teachings or may be acquired from practice of the methodologies set forth in the present disclosure.

Even though particular combinations of features and steps are recited in the claims and/or disclosed in the specification, these combinations are not intended to limit the disclosure. In fact, many of these features and steps may be combined in ways not specifically recited in the claims and/or disclosed in the specification. Although each dependent claim listed below may directly depend on only one other claim, the disclosure includes each dependent claim in combination with every other claim in the claim set.

Similarly, although each illustrative embodiment listed above may directly depend on only one other illustrative embodiment, the disclosure includes each illustrative embodiment in combination with every other illustrative embodiment in the set of illustrative embodiments for each mode of the inventive concepts disclosed herein.

No element, act, or instruction used in the present application should be construed as critical or essential to the disclosure unless explicitly described as such outside of the preferred embodiment. Further, the phrase "based on" is intended to mean "based, at least in part, on" unless explicitly stated otherwise.

What is claimed is:

1. A transducer array, comprising:

a transfer layer configured to transfer Tumor Treating Fields (TTFields) into a patient;

an electrode configured to emanate the TTFields, the electrode having a first side covered by the transfer layer and a second side opposite the first side and having a first portion and a second portion;

a temperature sensor in contact with the first portion of the second side of the electrode; and an isolation layer covering the temperature sensor and the first portion of the second side of the electrode but not disposed over the second portion of the second side of the electrode, such that the temperature sensor is positioned between the isolation layer and the first portion of the second side of the electrode, the isolation layer resisting heat flow through the isolation layer.

2. The transducer array of claim 1, wherein the isolation layer has an isolation thickness, the transducer array further comprising a top-coat layer disposed over the isolation layer and the second portion of the second side of the electrode not in contact with the temperature sensor and the isolation layer, the top-coat layer having a top-coat thickness that is thinner than the isolation thickness of the isolation layer.

3. The transducer array of claim 2, wherein the isolation thickness of the isolation layer is in a range of 2-6 times thicker than the top-coat thickness of the top-coat layer.

4. The transducer array of claim 2, wherein the isolation layer comprises a thermally insulating matrix material, the thermally insulating matrix material configured to resist heat flow from an atmosphere outside of the isolation layer to the temperature sensor, the isolation layer being more thermally insulating than the top-coat layer.

5. The transducer array of claim 1, wherein the isolation layer is a thermal insulator.

6. The transducer array of claim 1, wherein the isolation layer comprises a liquid resistant matrix material, the liquid resistant matrix material configured to resist a liquid flow through the isolation layer.

7. The transducer array of claim 6, wherein the isolation layer is hydrophobic.

8. The transducer array of claim 1, wherein the isolation layer is in contact with less than 20% of the second side of the electrode.

9. The transducer array of claim 1, wherein the isolation layer comprises at least one of an epoxy material, a thermally insulating foam material, and a hydrophobic material.

10. The transducer array of claim 1, wherein the isolation layer is non-conducting.

11. The transducer array of claim 1, wherein the isolation layer has a first insulation value, and wherein the electrode has an outer perimeter, and further comprising a non-conductive top-coat layer disposed on the isolation layer, the non-conductive top-coat layer extending within the outer perimeter and beyond the outer perimeter of the electrode, the non-conductive top-coat layer having a second insulation value less than the first insulation value.

12. The transducer array of claim 1, wherein the temperature sensor has a contact portion that is in contact with the first portion of the second side of the electrode and has an exposed portion not in contact with the second side of the electrode, and wherein the isolation layer surrounds the exposed portion of the temperature sensor and extends to the first portion of the second side of the electrode without contacting the second portion of the second side of the electrode.

13. A tumor treating field system, comprising:

an electric field generator configured to generate an electrical signal having an alternating current waveform at a frequency in a range from 50 kHz to 1 MHz;

a first conductive lead electrically coupled to the electric field generator, the first conductive lead configured to carry the electrical signal;

a first transducer array coupled to the first conductive lead, the first transducer array comprising:

an electrode layer having a first surface, a second surface opposite the first surface and having a first portion and a second portion, and an outer perimeter, the electrode layer comprising at least one electrode configured to receive the electrical signal from the electric field generator;

a transfer layer in contact with the first surface of the electrode layer;

a temperature sensor in contact with the first portion of the second surface of the electrode layer; and an isolation layer disposed over the temperature sensor and the first portion of the second surface of the electrode layer but not disposed over the second portion of the second surface of the electrode layer, the isolation layer resisting heat flow through the isolation layer;

a second conductive lead electrically coupled to the electric field generator; and a second transducer array coupled to the second conductive lead, the second transducer array receiving the electrical signal from the second conductive lead, and, in conjunction with the first transducer array, forming a tumor treating field.

14. The tumor treating field system of claim 13, wherein the isolation layer has an isolation thickness, wherein the first transducer array further comprises a top-coat layer disposed over the isolation layer and the second portion of the second surface of the electrode layer not in contact with the temperature sensor and the isolation layer, the top-coat layer having a top-coat thickness that is thinner than the isolation thickness of the isolation layer.

15. The tumor treating field system of claim 14, wherein the isolation layer comprises a thermally insulating matrix material, the thermally insulating matrix material configured to resist the heat flow from the temperature sensor to an atmosphere outside of the isolation layer more than that of the top-coat layer.

16. The tumor treating field system of claim 13, wherein the isolation layer has a first insulation value, and wherein the first transducer array further comprises a non-conductive top-coat layer disposed on the isolation layer, the non-conductive top-coat layer extending within the outer perimeter and beyond the outer perimeter of the electrode layer, the non-conductive top-coat layer having a second insulation value less than the first insulation value.

17. The tumor treating field system of claim 13, wherein the transfer layer is a non-conductive, thin-film polymer layer.

18. The tumor treating field system of claim 13, wherein the electrode layer of the first transducer array comprises a plurality of electrodes and a plurality of temperature sensors, each electrode comprising a first electrode surface and a second electrode surface opposite the first electrode surface, the second electrode surface having a first electrode portion and a second electrode portion larger than the first electrode portion, each electrode having a respective temperature sensor in contact with the first portion of the second electrode surface, and wherein the isolation layer includes a plurality of isolation sections with at least some of the isolation sections disposed over respective ones of the temperature sensors and the first portion of the second electrode surface of each electrode, but not disposed over the second portion of the second electrode surface.

19. The tumor treating field system of claim 13, wherein the isolation layer comprises a liquid resistant matrix material, the liquid resistant matrix material configured to resist a liquid flow through the isolation layer.

20. The tumor treating field system of claim 13, wherein the isolation layer is non-conducting.

* * * * *